United States Patent

Yoshida

[11] Patent Number: 5,242,299
[45] Date of Patent: Sep. 7, 1993

[54] ORTHODONTIC BRACKET

[75] Inventor: Masahiro Yoshida, Saitama, Japan

[73] Assignee: Hoya Corporation, Tokyo, Japan

[21] Appl. No.: 825,997

[22] Filed: Jan. 27, 1992

[30] Foreign Application Priority Data

Feb. 28, 1991 [JP] Japan .................... 2-7160[U]

[51] Int. Cl.$^5$ ................................ A61C 3/00
[52] U.S. Cl. ............................ 433/8; 433/10
[58] Field of Search ............... 433/8, 9, 10, 11, 13

[56] References Cited

U.S. PATENT DOCUMENTS

| | | | |
|---|---|---|---|
| 3,423,833 | 1/1969 | Pearlman | 433/8 X |
| 4,310,306 | 1/1982 | Wallshein | 433/9 X |
| 4,322,206 | 3/1982 | Reynolds | 433/8 X |
| 4,799,882 | 1/1989 | Kesling | 433/8 |
| 4,936,773 | 6/1990 | Kawaguchi | 433/8 X |
| 5,044,945 | 9/1991 | Peterson | 433/8 |
| 5,078,596 | 1/1992 | Carberry et al. | 433/8 |
| 5,160,261 | 11/1992 | Peterson | 433/8 |

Primary Examiner—Gene Mancene
Assistant Examiner—Nicholas D. Lucchesi
Attorney, Agent, or Firm—Ladas & Parry

[57] ABSTRACT

A dental orthodontic bracket is made from a body of a ceramic, a polymer or a composite thereof, the body having a longitudinal slot for an archwire formed by opposed upstanding wall portions on a base. The wall portions each have a pair of lateral wings at opposite end portions of the slot and an intermediate portion joining the wings. The wings have convex outer surfaces smoothly joined with a concave outer surface of the intermediate portion thereby forming a sinusoidal outline. The bottom surfaces of the wings form a clearance space with the base for a ligature wire clamp. The bottom of the slot is located above the bottom surfaces of the wings and the lowest point of the wings is at their tips. The upper surface of the wings is convex and the bottom surface concave.

11 Claims, 5 Drawing Sheets

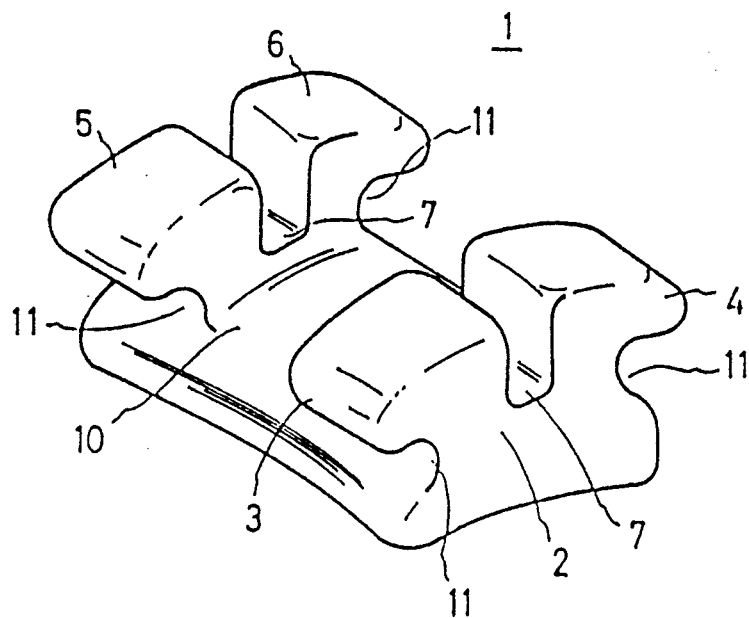
FIG. 5 *(Prior Art)*
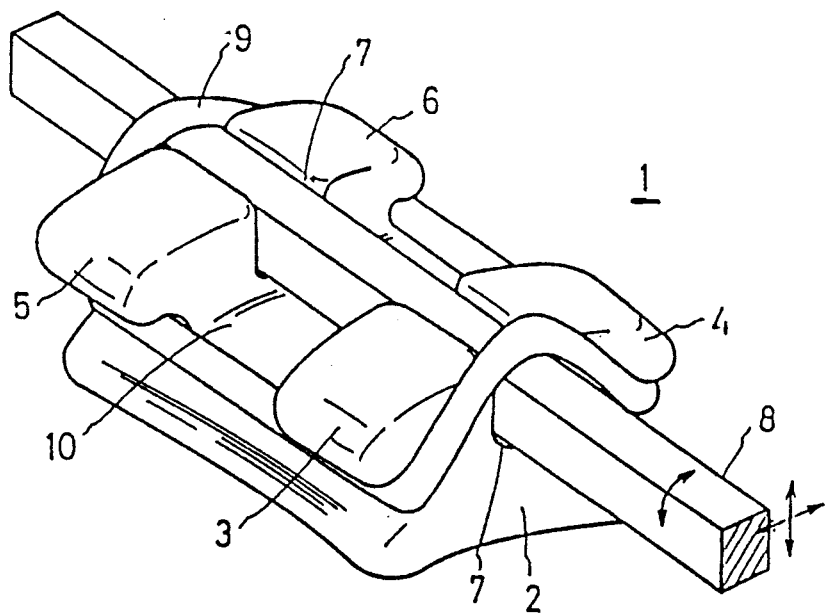
FIG. 6 *(Prior Art)*

FIG. 9 (a) (Prior Art)
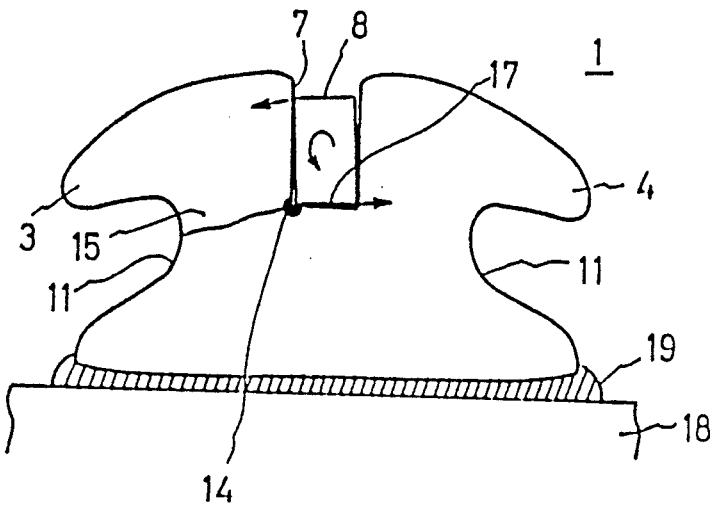
FIG. 9 (b) (Prior Art)
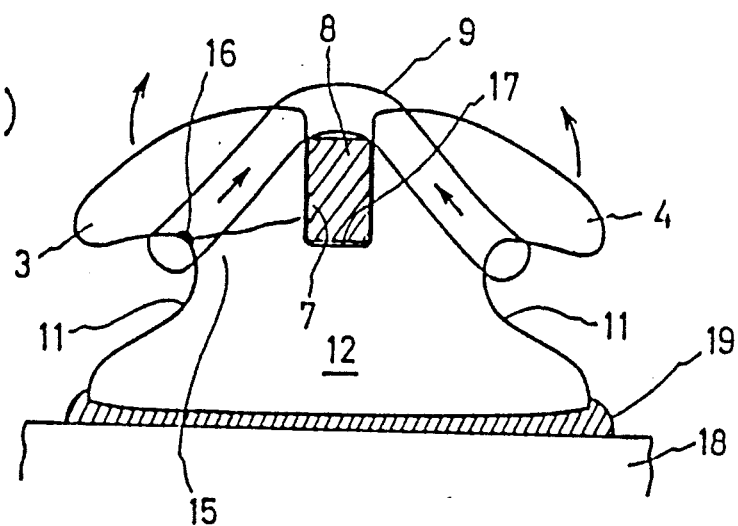

ORTHODONTIC BRACKET

BACKGROUND OF THE INVENTION

This invention relates to an orthodontic bracket for use in orthodontic therapy.

Conventionally, an orthodontic bracket is generally made of a metal material such as stainless steel or the like. FIGS. 5 and 6 show a conventional example of such an orthodontic bracket 1. A flat-shaped bracket base 2 is united with ligature wire clamping wings 3 to 6 of hook-shapes (L-shapes) at both ends of an upper surface of the bracket base back to back in an opposite manner and which number four in total. A thin metal wire (an archwire) 8 which clamps the orthodontic bracket 1 on a tooth surface is passed through narrow U-shaped slots 7,7 between the back-to-back opposite wings 3 and 4, 5 and 6. A thin wire (ligature wire) 9 is clamped to the ligature wire clamping wings 3 to 6 to fasten the archwire 8 in the slots 7,7. An upper surface of the bracket base 2 between the ligature wire clamping wings 3 to 6 is perpendicular to the slots 7,7 to form a groove 10 which has a width and a depth wider and somewhat deeper than the slots 7,7. A space between extremities of the ligature wire clamping wings 3 to 6 and the bracket base 2 form ligature wire clamping grooves 11 for clamping the archwire 8. Such a metallic orthodontic bracket 1 is excellent in strength and function but is disadvantageous in that it is conspicuous due to its metallic luster and is unattractive.

Recently, studies have been made regarding applications of various ceramics, polymers, and composites thereof to the bracket for purpose of improving its appearance. FIGS. 7 and 8 show a general configuration of an orthodontic bracket 12 which is made of such materials and which resembles the metallic bracket 1. However, it is to be noted that, a pair of slot-forming walls 13 which define slot 7 project continuously from the bracket base 2 over the entire length of the base in the direction of the ligature wire, and the groove 10 of the metallic bracket is generally omitted.

In use of the above orthodontic brackets 1 and 12, a bottom surface of the bracket base 2 is adhered and fixed to a surface of a tooth. The archwire 8, of a rectangular cross section, is passed through the slot 7 and fixed to the bracket base 2 by the ligature wire 9. With this construction, the teeth are subtly moved along the archwire 8 by applying a load such as torsion, bending, tension, or the like to the archwire 8 and by transmitting the load to the teeth. Accordingly, excessive friction between the inside surface of the slot and the surface of a wire surface reduces the efficiency of movement of the teeth and undesirably lengthens the treatment period.

Furthermore, the orthodontic bracket 12 of a nonmetallic material is weak in toughness and is subject to breakage and cracking during medical treatment in comparison with the metallic bracket of, for example, stainless steel. Various loads are applied to the orthodontic bracket 12 by the archwire 8, and the like. Main loads which cause the breakage to occur are classified into two categories as illustrated in FIGS. 9(a) and (b). In the load category as illustrated in FIG. 9(a), the stress tends to be concentrated at a corner 14 at the bottom of the slot due to reaction force caused by the torsion of the archwire 8. A crack is often produced from the corner 14 towards the bottom of the ligature wire clamping wing 3, namely, in narrow or waist portion 15. On the contrary, in the load category, illustrated in FIG. 9(b), the stress is liable to be concentrated at a bottom portion 16 on the lower surface of each ligature wire clamping wing 3 due to tension caused by the ligature wire 9. As a result, a crack is produced from the bottom portion 16 towards the slot 7. The fracture strength of the ligature wire clamping wing 3 is approximately proportional to the square of the distance between the corner 14 and the bottom portion 16 of the lower surface.

Another problem of the bracket 12 made of ceramic or polymer is that the efficiency of movement of the teeth is low and that a long period of time is required for medical treatment because the friction of the archwire 8 is larger than that with the metal bracket.

In addition, the bottom surface 17 of the slot 7 is substantially flush with the bottom portion of the lower surface in FIG. 9. In FIGS. 9a and 9b numeral 18 is a tooth and 19 is cement.

SUMMARY OF THE INVENTION

Accordingly, this invention is made in consideration of the above-mentioned problems and an object of this invention is to provide an orthodontic bracket made of a nonmetallic material, such as ceramic, polymer, and a composite thereof, which avoids the problems regarding cracks and breakage and wherein a good efficiency of movement of the teeth is accomplished.

According to a first aspect of the present invention, a dental orthodontic bracket is characterized by a bracket base having a pair of slot-forming walls, which extend in a lengthwise direction in an opposed manner on a center portion of the base with a continuous slot defined therebetween and ligature wire clamping wings projecting at end portions of an external side surface of each of the slot-forming walls. The bracket body and the wings are integrally formed of ceramic, polymer, or a composite thereof. The slot has a bottom located at a position higher than a bottom portion located on a lower surface of each ligature wire clamping wing. The external side surface of each slot-forming wall and inside surfaces of the wings disposed on both sides of said external side surface are contiguous to each other to form a continuous concave surface.

According to a second aspect of the present invention, the dental orthodontic bracket is characterized in that the upper surface of each ligature wire clamping wing has a convex surface such that a foundation side is located higher than the extremity of each wing.

According to a third aspect of the present invention, the dental orthodontic bracket is characterized by a recessed portion formed on at least one of the internal surfaces of the wall and the bottom of said slot.

According to a fourth aspect of the present invention, the dental orthodontic bracket is characterized in that the extremity poriton of each ligature wire clamping wing, is located at a position lower than the bottom portion of the lower surface of each ligature wire clamping wing.

In the present invention, the distance between the corner on the bottom surface of the slot and the bottom portion of the lower surface on each ligature wire clamping wing becomes large by locating the bottom surface of the slot at a position higher than the bottom portion of the lower surface on each ligature wire clamping wing. A continuous concave surface is formed by the external side surface of the slot-forming walls and the inside surfaces of each ligature clamping wing located on both sides of the external side surface. The width of a base or root portion of each wing is greater than that of an extremity of each wing. Each upper surface of the wings form a convex surface such that the base portion is higher than the extremity portion so as to lessen contact between the upper surfaces and the teeth, the tongue, or the lips. Further, the recessed portion formed on the slot serves to reduce the contact area of the frictional resistance between the archwire and the bracket. The extremities of the wings are bent downwards, which facilitates clamping the ligature wire.

BRIEF DESCRIPTION OF THE DRAWING

FIG. 5 is a perspective view of a conventional metal bracket;

FIG. 6 is a perspective view of the conventional metal bracket in its state of use;

FIGS. 9(a) and (b) are views for describing loads which are applied on the bracket illustrated in FIGS. 7 and 8.

DESCRIPTION OF THE PREFERRED EMBODIMENTS

Figure 1:
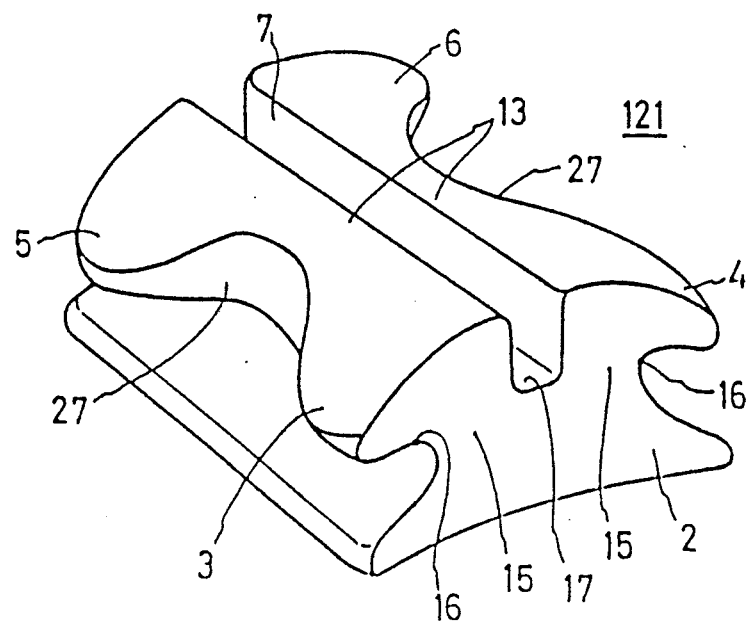
FIG. 1 is a perspective view of an orthodontic bracket according to an embodiment of this invention.

Description will next be made as regards a preferred embodiment of the present invention with reference to the drawing.

The bracket illustrated in FIGS. 1 through 4 comprises similar parts designated by like reference numerals as in FIGS. 5 through 9. Duplicate description of such parts will be omitted for the purpose of brevity. In these figures, the illustrated bracket 121 is made of yttria stabilized zirconia, polymethylmethacrylate, dental composite resin, and the like. The bracket is integrally formed by an injection molding technique or casting technique in which dental composite resin is cast into a silicon rubber die. The bracket comprises a bracket base 2, a pair of slot-forming walls 13 opposed to each other on the central upper surface of the bracket base 2 to define a slot 7 and ligature wire clamping wings 3-6 which project from and are united with both ends of the outside surface of each slot-forming wall 13. The bottom surface 17 of the slot 7 is located at a position higher than the bottom portion 16 of the lower surface of each wing 3-6 by a distance d (about 0.2 mm). Accordingly, a distance D, namely, the distance between the corner 14 of the bottom surface 17 of slot 7 and the bottom portion 16 of the lower surface of each wing 3-6 is 0.9 mm, compared to a conventional distance of about 0.7 mm. An excessive length of the distance d makes the height of the orthodontic bracket 12 undesirably high and is not preferable from a functional and handling aspect.

The waist portion 15 of the wings 3-6 has a width W between 1.9 mm and 2.5 mm. A width less than 1.9 mm makes the distance D small and the strength of the wings 3-6 weak. On the other hand, if the distance D is greater than 2.5 mm, the strength is good but the total size becomes excessively large. Therefore, preferable function and handling can not be expected. Each ligature wire clamping wing has a convex upper surface such that the surface at the root or bottom portion becomes higher than at the extremity. In addition, the extremity portion is lower than the root portion of the lower surface. The bottom portion 16 and the corner 14 of the slot 7 are defined by curved surfaces having radii of curvature of 0.2 mm and 0.1 mm, respectively, in order to alleviate concentration of stress.

Concave portions 23 and 24 are formed on the bottom surface 17 of the slot 7 and on one of the internal surfaces 21 (FIGS. 2 and 4), respectively, in order to reduce the contact area between the archwire 8 and the slot 7. The depth w of the concave portions 23 and 24 falls within a range between 10 and 200 micrometers. Preferably, the depth is between 30 and 100 micronmeters. In addition, a number of concave portions 23 and 24 may be provided. If a plurality of concave portions are uniformly distributed lengthwise along the slots 7, the load imposed on the slot 7 by the archwire and the ligature wire can be equally distributed.

While the concave portion 24 is shown only on one of the internal surfaces 21, it is also formed on the other internal surface 25.

The external surface of each slot-forming wall 13 may be contiguous to the inside surfaces defined by the wings 3 and 5 or by wings 4 and 6 and has a concave surface 27 of determined radius R of curvature (for example, R=0.8 mm). By forming concave portion 27, the width of the root or bottom portions of the wings 3-6 is greater than the width of the extremity portions.

Figure 2:
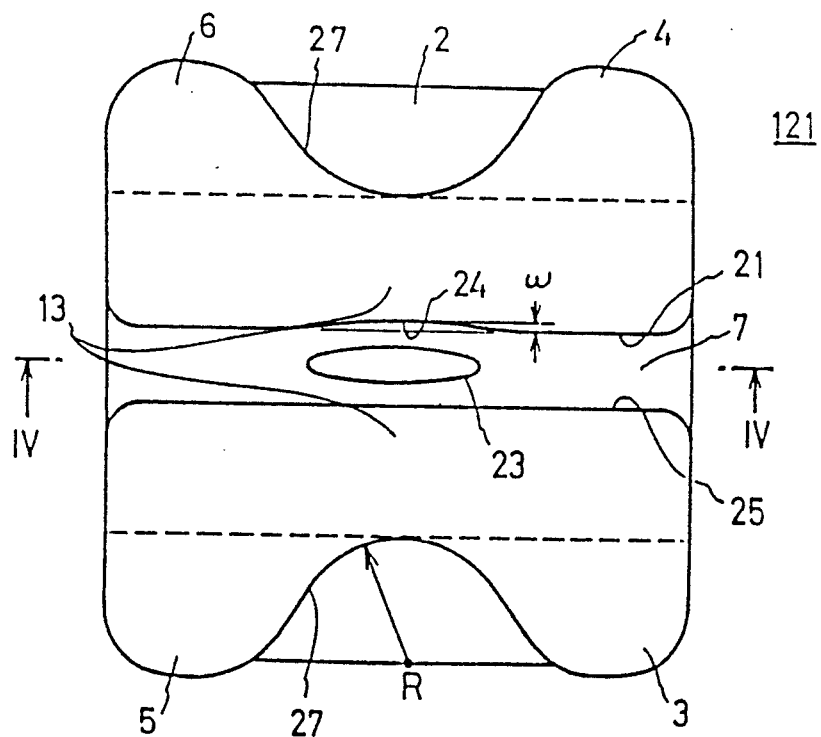
FIG. 2 is a plan view of the orthodontic bracket shown in FIG. 1.

In effect, a sinusoidal outline is formed, as shown in FIG. 2, by the outer extremity of the wings of each pair and the concave surface 27 at the intermediate portion of the walls 13 connecting the wings.

In the orthodontic bracket 121 having the structure as mentioned above, the distance D between the corner 14 on the bottom surface 17 and the bottom portion 16 of the lower surface of each wing 3-6 becomes large by locating the bottom surface 17 of the slot 7 at a position higher than the bottom portion 16 of each wing 3-6 by the distance d. In addition, the width of the waist portion 15 is also increased. As a result, the strength of each wing 3-6 is increased and no cracking is caused at the corner 14 of the bottom surface 17 and the bottom portion 16 of the lower surface. This enables alleviation and prevention of cracking and breakage during the medical treatment.

Figure 3:
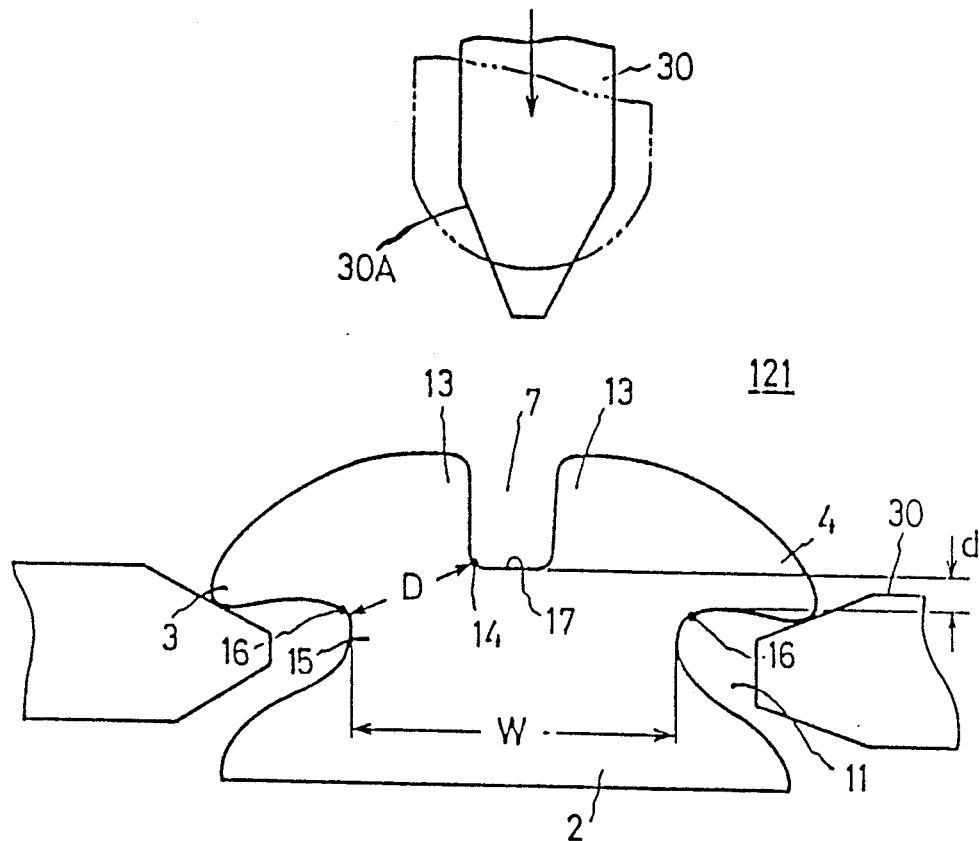
FIG. 3 is a side view of the orthodontic bracket shown in FIG. 1.
Figure 4:
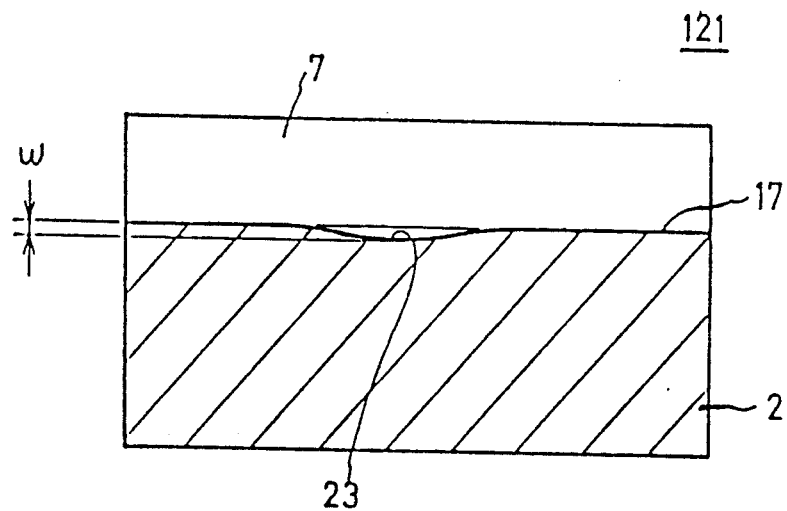
FIG. 4 is a sectional view taken along line IV—IV in FIG. 2.
Figure 7:
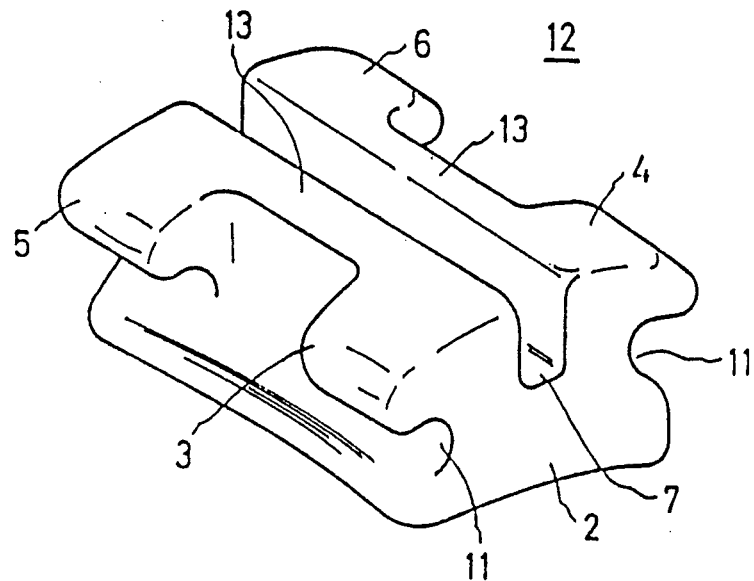
FIG. 7 is a perspective view of a conventional ceramic bracket.
Figure 8:
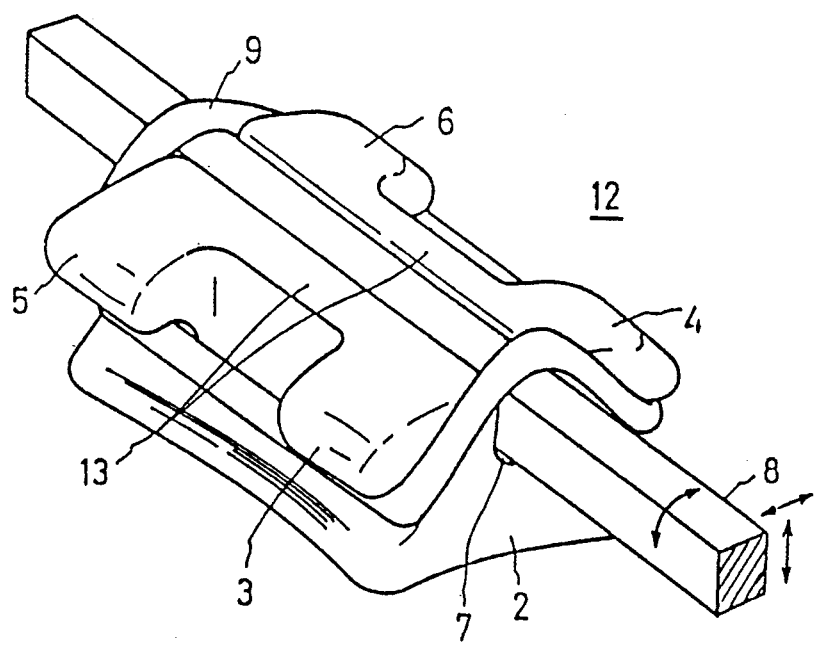
FIG. 8 is a perspective view showing the conventional ceramic bracket in its state of use.

Testing to breakage was performed in two different ways: in the first a wedge-shaped test piece 30 was downwardly inserted in the slot 7 as shown in FIG. 3; in the second the upper surface of the bracket was loaded by a circular test piece 30A, shown in chain-dotted lines. Under the circumstances, the wings 3-6 were supported by test pieces 30 transversally inserted in slots 11. As a result of the two tests, the wings of a conventional bracket shown in FIG. 7 were broken at a load of 14 kg and 15 kg, respectively. On the contrary, breakage of the wings of the bracket according to the present invention was produced under loads of 24 kg and 33 kg, respectively. In this event, the test was made with the bracket adhered to a metal plate.

As mentioned above, each wing has a convex upper surface such that the extremity portions are located at positions lower than the bottom side portions. In addition, each wing becomes thinner as it approaches the extremity. The bracket rarely contacts the teeth and lips. Accordingly, it is possible to prevent the wings 3–6 from undergoing cracking, breakage, or abrasion and to improve durability of the bracket 121. As mentioned previously, a bracket of ceramic or polymer generally has the deficiency that the teeth are not effectively moved because the friction between the slot and the archwire is large as compared to a metal bracket. However, the bracket according to the present invention provides the concave portions 23 and 24 on the walls of the slot 7 so that the contact area between the archwire and the bracket 121 can be reduced. As a result, the efficiency of movement of the teeth can be improved, which is advantageous because the medical treatment period is shortened. The friction between the bracket and the archwire was measured. The resulting movement load was 35 g in the conventional bracket illustrated in FIG. 7 and was 23 g in the bracket of the present invention. The movement load was given by the force which is required for moving the bracket when the bracket was pushed down with a weight of 100 g and was pulled along the longitudinal axis of the archwire.

As mentioned above, the orthodontic bracket according to the present invention is made of ceramic, polymer, or a composite thereof, and is therefore not conspicuous as compared with a metallic bracket. In addition, the width of the waist portion is enlarged by locating the bottom surface of the slot at a position higher than the bottom portion of the lower surface of each wing. The surface defined by the external surface of the slot-forming wall and the inside surface of each wing is formed as a contiguous concave surface and the width of the bottom portion of each wing is greater than that of the extremity portion. As a result, the fracture strength of the bracket is increased. Accordingly, it is possible to prevent the bracket from cracking or breaking on installation and during the medical treatment period. Further, each wing has the convex upper surface such that the extremity portions are located at positions lower than the bottom side portions. The bracket rarely contacts the teeth and lips. The abrasion of the bracket and the teeth can thereby be reduced. The labium superius oris and the lingua will not be abraded by the bracket and vulnus in the cavitas oris will not be produced. Further, the friction is reduced between the archwire and the bracket by providing the concave inside surface of the slot. As a result, the efficiency of movement of the teeth can be improved, which is advantageous in that the medical treatment period is shortened. Because the extremity portion of each wing is located at a position lower than the bottom portion thereof. The ligature is prevented from being separated from the slot because the ligature is positively fastened.

What is claimed is:

1. A dental orthodontic bracket for use in orthodontic therapy, said bracket comprising:
    a body made from a material selected from the group consisting of ceramics, polymers and composites thereof, said body comprising:
    a base,
    a pair of upstanding opposed portions on said base defining a longitudinal slot for passage of an archwire therethrough, said longitudinal slot having an open top, a pair of facing side walls and a bottom surface joined to said side walls,
    each of said upstanding portions including a pair of wings extending laterally of said slot at opposite ends of said longitudinal slot and joined together by an intermediate portion having a curved, outer concave surface which smoothly merges with a rounded outer edge surface of each of said wings,
    each of said wings having a lower surface forming a clearance space with said base for passage of a ligature wire clamp therethrough, and an upper convex surface,
    said bottom surface of said slot being at a higher level than said lower surfaces of said wings, said lower surface of each wing being curved and extending downwardly towards said base in a direction away from said slot so that the lowest point of the wing is at the lateral extremity thereof,
    said wings each having a thickness measured between said upper and lower surfaces thereof, the thickness of each said wing diminishing as the wing extends laterally away from said slot,
    said wings having a width measured in the longitudinal direction of said slot which decreases as the wing extends laterally away from said slot.

2. A dental orthodontic bracket as claimed in claim 1, wherein said rounded outer edge surfaces of said wings are convex.

3. A dental orthodontic bracket as claimed in claim 1, wherein said side walls of said slot are joined to said bottom surface thereof by rounded corners having determined radii of curvature.

4. A dental orthodontic bracket as claimed in claim 3, wherein said radii of curvature are each 0.1 mm.

5. A dental orthodontic bracket as claimed in claim 1, wherein said bottom surface of said slot has a recessed portion with a depth of between 10 and 200 micronmeters.

6. A dental orthodontic bracket as claimed in claim 1, wherein at least one of said side walls of said slot has a recessed portion with a depth between 10 and 200 micronmeters.

7. A dental orthodontic bracket as claimed in claim 1, wherein said concave surface has a radius of curvature of 0.8 mm.

8. A dental orthodontic bracket as claimed in claim 1, wherein said lower surface of each wing has a radius of curvature of 0.2 mm.

9. A dental orthodontic bracket as claimed in claim 1, wherein said curved lower surface of each wing smoothly merges with a curved outer surface of said base to form said clearance space.

10. A dental orthodontic bracket as claimed in claim 1, wherein said longitudinal slot has rounded entry surfaces at opposite ends of the slot.

11. A dental orthodontic bracket as claimed in claim 1, wherein said rounded outer edge surfaces of said wings and said outer concave surface of said intermediate portion define a sinusoidal outline.

* * * * *